United States Patent
Chaney et al.

(10) Patent No.: US 12,313,626 B2
(45) Date of Patent: May 27, 2025

(54) METHODS FOR DETECTING HOOK EFFECT(S) ASSOCIATED WITH ANAYLTE(S) OF INTEREST DURING OR RESULTING FROM THE CONDUCTANCE OF DIAGNOSTIC ASSAY(S)

(71) Applicant: Siemens Healthcare Diagnostics Inc., Tarrytown, NY (US)

(72) Inventors: Julie Chaney, Elkhart, IN (US); Jon Stradinger, Kalamazoo, MI (US); Aaron Kauffmann, Elkhart, IN (US); Jeffrey Mayfield, South Bend, IN (US); Chris Zimmerle, Goshen, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1099 days.

(21) Appl. No.: 17/279,958

(22) PCT Filed: Sep. 20, 2019

(86) PCT No.: PCT/US2019/052093
§ 371 (c)(1),
(2) Date: Mar. 25, 2021

(87) PCT Pub. No.: WO2020/068574
PCT Pub. Date: Apr. 2, 2020

(65) Prior Publication Data
US 2021/0389307 A1    Dec. 16, 2021

Related U.S. Application Data

(60) Provisional application No. 62/738,401, filed on Sep. 28, 2018.

(51) Int. Cl.
| | | |
|---|---|---|
| *G01N 33/53* | (2006.01) | |
| *G01N 21/27* | (2006.01) | |
| *G01N 21/78* | (2006.01) | |
| *G01N 21/82* | (2006.01) | |
| *G01N 33/543* | (2006.01) | |

(52) U.S. Cl.
CPC ....... *G01N 33/5306* (2013.01); *G01N 21/272* (2013.01); *G01N 21/78* (2013.01); *G01N 21/82* (2013.01); *G01N 33/54393* (2013.01); *G01N 2021/825* (2013.01); *G01N 2333/76* (2013.01)

(58) Field of Classification Search
None
See application file for complete search history.

(56) References Cited

U.S. PATENT DOCUMENTS

| | | |
|---|---|---|
| 4,990,075 A | 2/1991 | Wogoman |
| 5,084,397 A | 1/1992 | Siddons et al. |
| 5,162,237 A | 11/1992 | Messenger et al. |
| 5,272,093 A | 12/1993 | Silva et al. |
| 5,610,073 A | 3/1997 | Chu et al. |
| 10,928,410 B2 | 2/2021 | Kauffmann |
| 2004/0029177 A1 | 2/2004 | Nadaoka et al. |
| 2010/0311185 A1 | 12/2010 | Schelp et al. |
| 2012/0015450 A1 | 1/2012 | Hasegawa et al. |
| 2012/0040470 A1 | 2/2012 | Dorn et al. |
| 2016/0161480 A1 | 6/2016 | Hegel et al. |
| 2016/0202271 A1 | 7/2016 | Yue et al. |
| 2018/0236448 A1 | 8/2018 | Linder et al. |

FOREIGN PATENT DOCUMENTS

| | | | |
|---|---|---|---|
| JP | S63149564 A | 6/1988 | |
| JP | H04204378 A | 7/1992 | |
| JP | H0593725 A | 4/1993 | |
| JP | H0694717 A | 4/1994 | |
| JP | H06109740 A | 4/1994 | |
| JP | H10282099 A | 10/1998 | |
| JP | H11264820 A | 9/1999 | |
| JP | H11264821 A | 9/1999 | |
| JP | 2000146975 A | 5/2000 | |
| JP | 2002214237 A | 7/2002 | |
| JP | 2016530514 A | 9/2016 | |
| WO | 2011016326 A1 | 2/2011 | |
| WO | 2013078130 A1 | 5/2013 | |
| WO | 2014/149111 | * 9/2014 | ............ G01N 33/53 |
| WO | 2018017332 A1 | 1/2018 | |
| WO | 2019055627 A1 | 3/2019 | |
| WO | 2020013970 A1 | 1/2020 | |

OTHER PUBLICATIONS

International Search Report and Written Opinion of International Application No. PCT/US2019/052093 dated Dec. 6, 2019.
European Search Report and Written Opinion of European Application No. 19866311.4 dated Sep. 27, 2021.
Roche: "cobas 6000 compendium", Jan. 1, 2005 (Jan. 1, 2005), URL: http://e-dok.rm.dk/C125702200417027/$CXIV/ERAN7T6ANT4/$File/COBI-CD%20-%20-%20cobas%206000%20%20EN.pdf, pp. 1-162.

* cited by examiner

*Primary Examiner* — Nora M Rooney (57) ABSTRACT

Devices and methods for the hook effect detection associated with analytes of interest in the conductance of one or more diagnostic assays, including, without limitation, immunoassays.

20 Claims, 2 Drawing Sheets

| Concentration | ≤ 350 mg/L | ≥ 2500 mg/L |
|---|---|---|
| Samples | 464 | 218 |
| Hook Effect | N/A | 161 |
| Flagged by Hook Detection Method | 0 | 218 |

| Concentration (mg/L) | Samples | Results < 500 mg/L | Flagged by Hook Detection |
|---|---|---|---|
| 1000 | 17 | 0 | 3 |
| 2000 | 16 | 16 | 16 |

FIG. 5

METHODS FOR DETECTING HOOK EFFECT(S) ASSOCIATED WITH ANAYLTE(S) OF INTEREST DURING OR RESULTING FROM THE CONDUCTANCE OF DIAGNOSTIC ASSAY(S)

CROSS REFERENCE TO RELATED APPLICATIONS

The subject application claims benefit under 35 USC § 119(e) of U.S. provisional Application No. 62/738,401, filed Sep. 28, 2018. The entire contents of the above-referenced patent application are hereby expressly incorporated herein by reference.

STATEMENT REGARDING FEDERALLY FUNDED RESEARCH OR DEVELOPMENT

Not Applicable.

TECHNICAL FIELD

The presently disclosed and claimed inventive concept(s) relate to a device(s), kit(s), and method(s) for detecting the concentration(s) of various analytes of interest which may be present in a patient's liquid test sample during the conductance of at least one diagnostic assay. More specifically, the presently disclosed and claimed inventive concept(s) relate to an improved method(s) for detecting the presence of microalbumin hook effect(s) during the conductance of microalbumin-to-creatinine ratio diagnostic assay(s) on a patient's urine test sample for the diagnosis of various health-related conditions, including, without limitation, kidney disease, diabetes, and/or hypertension.

BACKGROUND

Numerous devices, kits, and methods exist for conducting assays that detect analytes that may be present in a patient's liquid test sample. Such devices and methods have proven to be effective in diagnostic assays that detect the presence, quantity, and/or concentration of certain analytes of interest indicative of a patient's health, including, but not limited to, glycated hemoglobin (HbA1c), microalbumin and creatinine, and lipid-based analytes, such as cholesterol, triglycerides, and/or high-density lipoproteins. It is common that such devices conduct diagnostic assays, including, without limitation, immunoassays, to either detect and/or measure the concentration of at least one analyte of interest present in a patient's liquid test sample (for instance, by way of example only, a patient's urine sample).

Figure 1:
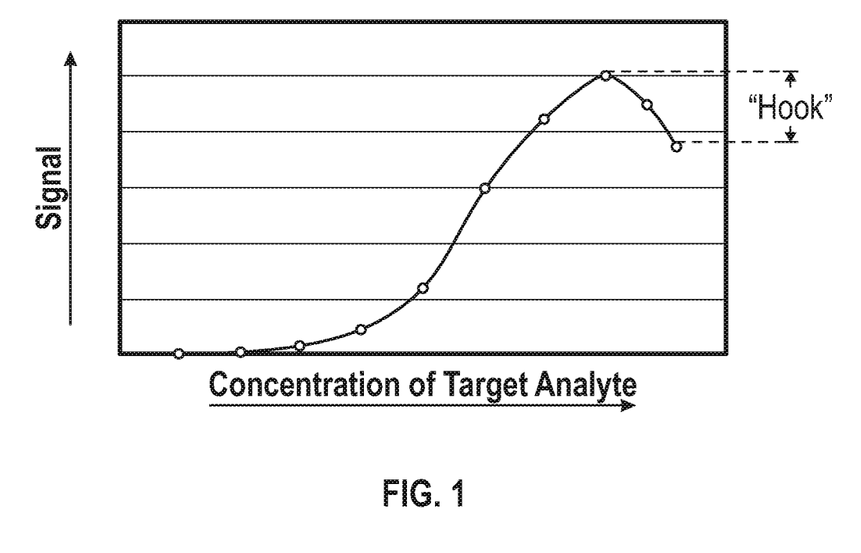
FIG. 1 is a graphical representation demonstrating a high-dose hook effect type of interference observed in immunoassays when a high concentration of a target analyte is present.

Immunoassays technologies are widely used in the field of medical diagnostics, and, in particular, with point of care analyzers that rely on absorbance-based measurement, such as, by way of example only, the DCA VANTAGE® analyzers commercially offered for sale by Siemens Medical Solutions USA, Inc., Malvern, PA In particular, these assays are useful in the detection of various protein analytes present in a patient's liquid test sample. Despite their widely accepted use in this field, various types of interferences are still observed when using these assays. For example, limitations in the detection range of immunoassay analyzers contribute to the phenomenon known as the "hook effect." The hook effect is observed when high target analyte concentrations in a patient's liquid test sample actually cause a decrease in the assay response signal for the target analyte, thereby resulting in the reporting of false negative or false low concentration results (see, for example, FIG. 1).

The hook effect is based on the saturation curve of antibody with antigen (again, see, for example, FIG. 1) and occurs when the concentration of target analyte in a patient's liquid test sample exceeds the binding capacity of the antibodies used in the assay reagents, thereby resulting in incomplete formation of the immune complexes required for creation of a response signal. For instance, excessively large concentrations of target analyte(s) (for instance, by way of example only, microalbumin and/or creatinine) can simultaneously saturate both capture and detection antibodies used in an immunoassay, thereby resulting in the "hook" or falsely decreased concentration measurement shown in FIG. 1. In these instances, false negative or false low results are reported, which negatively impacts the accuracy of the analyzer and can have extremely deleterious consequences on patient care.

In order to compensate for the hook effect, health care providers and users are advised to utilize secondary mechanisms, such as, by way of example, a reaction test strip or the addition of a wash step in between the incubation of the patient's liquid test sample with the capture antibody and the subsequent addition of the detection antibody, to determine the true concentration of an analyte of interest in those samples suspected of containing extremely high concentrations of a target analyte(s) of interest, for instance, by way of example, a target peptide and/or protein. However, these secondary mechanisms require additional time, money, and machinery to accomplish. Accordingly, there is a need for an improved assay method that mitigates and/or eliminates the inaccuracies introduced by the hook effect during the conductance of one or more assays. It is to such devices and methods that the presently disclosed and/or claimed inventive concept(s) are directed.

DETAILED DESCRIPTION

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example, but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. The volume of the sample utilized in accordance with the presently disclosed and claimed inventive concept(s) is from about 0.1 to about 100 microliters. As used herein, the term "volume" as it relates to the liquid test sample utilized in accordance with the presently disclosed and claimed inventive concept(s) means from about 0.1 microliter to about 100 microliters, or from about 1 microliter to about 75 microliters, or from about 2 microliters to about 60 microliters, or less than or equal to about 50 microliters, or less than or equal to about 40 microliters. In one non-limiting embodiment of the presently disclosed and/or claimed inventive concept(s), the liquid test sample is about 40 microliters of urine.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

The term "reaction vessel" includes any device(s) capable of performing at least one diagnostic assay as described herein, including devices for performing diagnostic assays, including, without limitation, immunoassays. The reaction vessel may perform the diagnostic assay(s) manually, but, in most instances, the reaction vessel will be inserted into a system that automates the performance of the diagnostic assay(s). In one non-limiting embodiment, the reaction vessel comprises a reaction cassette for use in automated diagnostic assays conducted by the DCA Vantage® Analyzer commercially available from Siemens Healthcare Diagnostics, Inc. Embodiments of a reaction vessel for use in combination with the DCA Vantage® analyzers and methods of use related thereof which are capable of accomplishing the presently disclosed and/or claimed inventive concept(s) are described in, by way of example only: U.S. Pat. No. 4,990,075 which issued on Apr. 11, 1988 and is currently owned by Siemens Healthcare Diagnostics Inc.; U.S. Pat. No. 5,084,397 which issued pm Jan. 28, 1992 and is currently owned by Siemens Healthcare Diagnostics, Inc.; U.S. Pat. No. 5,162,237 which issued on Nov. 10, 1992 and is currently owned by Siemens Healthcare Diagnostics, Inc.; U.S. Pat. No. 5,272,093 which issued on Dec. 21, 1993 and is currently owned by Siemens Healthcare Diagnostics, Inc.; U.S. Patent U.S. Pat. No. 5,610,073 which issued on Mar. 11, 1997 and is currently owned by Siemens Healthcare Diagnostics, Inc.; International Application Serial No. PCT/US2017/-40909 which was filed on Jul. 6, 2017 and is currently owned by Siemens Healthcare Diagnostics, Inc.; U.S. patent application Ser. No. 15/970,272 which was filed on May 3, 2018 and is currently owned by Siemens Healthcare Diagnostics, Inc.; International Application Serial No. PCT/US2018/050839 which was filed on Sep. 13, 2018 and is currently owned by Siemens Healthcare Diagnostics, Inc.; and U.S. Provisional Application Ser. No. 62/697,672 which was filed on Jul. 13, 2018 and is currently owned by Siemens Healthcare Diagnostics, Inc. The entire contents of each of the above-referenced patents and patent application are expressly incorporated in their entirety herein by reference. While the above referenced patents all describe embodiments of reaction vessels and systems owned by Siemens Healthcare Diagnostics, Inc., a person having ordinary skill in the art should readily appreciate that the presently disclosed and/or claimed inventive concept(s) can be utilized on any diagnostic assay system that conducts at least one diagnostic assay on a patient's liquid test sample.

Any of the method steps described herein may be performed, including, but not limited to, by a user. However, as used herein, the term "user" is not limited to use by a human being. Rather, the term "user" may comprise by way of example only, and not by way of limitation, a computer, a server, a website, a processor, a network interface, a human, a user terminal, a virtual computer, combinations thereof, and the like.

The various embodiments of the presently disclosed and/or claimed inventive concept(s) may be utilized with any reflectance and/or reflectance-based spectroscopic diagnostic instrument that is capable of (or has been modified to be capable of) functioning in accordance with the methods described herein. In certain non-limiting embodiments, the instrument may be a point of care instrument. The reflectance spectroscopic diagnostic instrument may be a system or systems that are able to embody and/or execute the logic of the methods/processes described herein. Logic embodied in the form of software instructions and/or firmware may be executed on any appropriate hardware. For example, logic embodied in the form of software instructions and/or firmware may be executed by one or more components of a dedicated system or systems, on a personal computer system, on a distributed processing computer system, and/or the like. In some embodiments, the entire logic may be implemented in a stand-alone environment operating on an instrument (such as, by way of example only, a point of care instrument). In other embodiments, the logic may be implemented in a networked environment such as a distributed system in which multiple instruments collect data that is transmitted to a centralized computer system for analyzing the data and supplying the results of the analysis to the instruments. Each element of the instrument may be partially or completely network-based or cloud-based, and may or may not be located in a single physical location.

Circuitry used herein includes, but is not limited to, analog and/or digital components, or one or more suitably-programmed processors (for example, microprocessors) and associated hardware and software, or hardwired logic. Also, "components" may perform one or more functions. The term "component" may include hardware, such as, by way of example only, a processor (e.g., microprocessor), an application specific integrated circuit (ASIC), field programmable gate array (FPGA), a combination of hardware and software, and/or the like.

Software utilized herein may include one or more computer readable medium (i.e., computer readable instructions) that when executed by one or more components cause the component to perform a specified function. It should be understood that the detection formula(s)/algorithm(s) described herein may be stored on one or more non-transient memory. Non-limiting exemplary non-transient memory may include random access memory, read only memory, flash memory, combinations thereof, and/or the like. Such non-transient memory may be electrically-based, optically-based, and/or the like.

The terms "hook effect detection formula(s)" and/or "hook effect detection algorithm(s)" as used herein means a mathematical equation and/or conditional statement and/or a series of mathematical equations and/or conditional statements that, when satisfied, is/are indicative of the presence of a patient's liquid test sample exhibiting the hook effect. Such hook detection formula(s) may be stored in the non-transient memory of, for instance, by way of example only, a diagnostic assay analyzer or, if a distributed system is utilized, a computer and/or computer system that is configured to be in functional communication with the diagnostic assay analyzer such that the computer and/or computer system may receive raw data and measurements from the analyzer for post-processing analysis. In one non-limiting embodiment of the presently disclosed and/or claimed inventive concept(s), the hook effect detection formula(s)/algorithm(s) is/are stored in the non-transient memory of a diagnostic assay analyzer. Upon receiving the raw data (such as, by way of example only, raw absorbance and/or concentration associated with at least one target analyte of interest present in the patient's liquid test sample) from various hardware components of the analyzer (including, without limitation, cameras, imagers, biosensors, and the like), the raw data is processed (for instance, by way of example only, by a microprocessor(s)) into at least one concentration result indicative of the concentration of the at least one target analyte of interest. Following processing and calculation of the at least one concentration result, the result is accessed by the non-transient memory of the diagnostic assay analyzer such that the at least one hook effect detection formula(s)/algorithm(s) stored therein utilizes the processed result to determine presence of hook effect interference associated with the at least one target analyte of interest present within the patient's liquid test sample. This information, as well as any other analytical details associated with the patient's liquid test sample, is then output, transmitted, and/or displayed, for instance, by way of example only, on at least one computer monitor of a healthcare provider for additional analyses, testing, diagnoses, and the like.

The presently disclosed and/or claimed inventive concept(s) contemplate that the variables, constants, equations, and/or conditional statements comprising the hook detection formula(s)/algorithm(s) are not stagnant and it/they may be modified (including any and/or all components thereof) to accomplish the presently disclosed and/or claimed inventive concept(s), including, without limitation, determining whether a patient's liquid test sample exhibits hook effect interference. In one non-limiting embodiment, the predetermined variables of the hook detection formula(s)/algorithm(s), such as, by way of example only (and described in further detail hereinbelow), the threshold values associated with the maximum target analyte concentration and reaction kinetics limit(s) may be set by a user during calibration.

In one non-limiting embodiment of the presently disclosed and/or claimed inventive concept(s), the hook detection formula/algorithm is represented by the following equation(s), variables, and conditional statement(s):

IF (Target Analyte Concentration is $\geq C$) AND $((MCR-MR2)/(MR2-MR1)>R)$, THEN Hook Effect [1]

wherein C represents the predetermined target analyte concentration threshold for the particular assay being performed; MR1 is a first absorbance reading taken of the target analyte at a first time ($T_1$); MR2 is a second absorbance reading taken of the target analyte at a second time ($T_2$); MCR is the final measured absorbance of the target analyte at the conclusion of the diagnostic assay; and R is a predetermined limit for the ratio value to assess the reaction kinetics of the assay. Alternatively (or in addition to), the hook detection formula(s)/algorithm(s) may comprise the following equation(s), variables, and conditional statements:

IF (Target Analyte Concentration is $\geq C$) AND $(MR1/MR2)>R$, THEN Hook Effect [2]

wherein C represents the predetermined target analyte concentration threshold for the particular assay being performed; MR1 is a first absorbance reading taken of the target analytes at a first time ($T_1$); MR2 is a second absorbance reading of the target analyte a second time ($T_2$); and R is a predetermined limit for the ratio value to assess the reaction kinetics of the assay.

The predetermined target analyte concentration threshold/result (represented hereinabove as constant C in hook detection formulas/algorithms [1] ad [2]) may be any concentration capable of accomplishing the presently disclosed and/or claimed inventive concept(s), including, without a limitation, any concentration of the target analyte within a range of from about 50 milligrams/liter to about 700 milligrams/liter, or from about 100 milligrams/liter to about 600 milligrams/liter, or from about 200 milligrams/liter to about 500 milligrams/liter, or from about 300 milligrams/liter to about 400 milligrams/liter. In one non-limiting embodiment of the presently disclosed and/or claimed inventive concept(s), the predetermined target analyte concentration threshold/result is about 200 milligrams/liter. In one non-limiting embodiment of the presently disclosed and/or claimed inventive concept(s), the predetermined target analyte concentration threshold/result is about 300 milligrams/liter. In one non-limiting embodiment of the presently disclosed and/or claimed inventive concept(s), the predetermined target analyte concentration threshold/result is about 500 milligrams/liter.

It is common in the field of diagnostic assays (such, as, by way of example, immunoassays) that such diagnostic assays comprise a "reporting range," wherein the reporting range (with respect to the concentration of a target analyte of interest) has both a lower reporting/detection limit (such as, by way of example, about 5 milligrams/liter) and an upper reporting/detection limit (such as, by way of example, about 300 milligrams/liter). The lower and upper limits of a diagnostic assay's reporting range may vary widely depending on, for instance, the chemistry and detection methodology(-ies) associated with particular diagnostic assay. The upper limit of a reporting range of a diagnostic assay can be utilized to generate a "flag" that indicates a potentially erroneous concentration measurement (as the reported concentration is outside the reporting range of the diagnostic assay). In one non-limiting embodiment of the presently disclosed and/or claimed inventive concept(s), a sample and/or result may be "flagged" by a diagnostic assay analyzer, the flag being indicative that the patient's liquid test sample (e.g., urine sample) contains a concentration of a target analyte of interest (e.g., microalbumin) that exceeds the upper limit of the diagnostic assay's reporting range, thereby confirming, or at least suggesting, the presence of hook effect intereference.

Thereafter, the erroneous concentration result(s) can be subsequently accounted for and corrected. For instance, an output can be sent to a user notifying the user that the at least one result of the detection formula indicates that the at least one target analyte of interest is subject to the hook effect. Accordingly, the user may thereafter perform subsequent analyses on the patient's liquid test sample to determine an accurate concentration of the at least one target analyte of interest present in the patient's liquid test sample (for instance, by way of example only, via conducting a secondary analysis utilizing a reaction strip(s) to confirm the accurate concentration of the at least one target analyte of interest).

Turning now to particular embodiments, the presently disclosed and claimed inventive concept(s) relate to a device(s), kit(s), and method(s) for determining whether a target analyte(s) of interest present in a patient's liquid test sample exhibits or is exhibiting the hook effect. More specifically, the presently disclosed and claimed inventive concept(s) relate to an improved method that utilizes a detection formula/algorithm for calculating whether the concentration of a target analyte(s) of interest (such as, way of example only, microalbumin protein) present within a patient's liquid test sample (for instance, a patient's urine sample) is accurate or inaccurate due to the hook effect.

It is contemplated that virtually any reagent used in the fields of biological, chemical, or biochemical analyses and assays could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a fluid sample can be used in the devices, kits, and methods of the presently claimed and inventive concepts. A variety of assays for detecting analytes are well known in the art and include, but are not limited to, chemical assays, enzyme inhibition assays, antibody stains, latex agglutination, latex agglutination inhibition and immunoassays, such as, radioimmunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the presently disclosed and claimed inventive concept(s) are not strictly limited to immunoassays and may include, by way of example and not by limitation, chemical and chemical-based assays, nucleic acid assays, lipid-based assays, and serology-based assays. Immunoassays, including radio-immunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbent assays (ELISAs) can be used in the presently claimed and disclosed inventive concepts, as well. In the case of an enzyme immunoassay, an enzyme is typically conjugated to a second antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and claimed inventive concept(s) to one skilled in the art.

Assays, including, but not limited to, immunoassays, nucleic acid capture assays, lipid-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, $\alpha$-1-microglobin, immunoglobins, enzymes, proteins, glycoproteins, protease inhibitors, drugs, cytokines, creatinine, and glucose. The device(s), kit(s), and method(s) disclosed and/or claimed herein may be used for the analysis of any liquid test sample, including, without limitation, whole blood, plasma, serum, or urine. In one non-limiting embodiment, the liquid test sample is about 40 microliters of urine.

The reagents utilized in accordance with the presently disclosed and/or claimed inventive concept(s) may be provided in any form and/or formulation that will allow them to function in accordance with the presently disclosed and/or claimed inventive concept(s). For example, and not by way of limitation, it may be desirable to dispose the reagents in the form of single use reagents. In addition, it may be desirable to lyophilize one or more of the reagents. The use of dried reagents in reaction vessels (such as, by way of example, immunoassay devices) is described in detail in International Patent Application Publication No. WO 2013/078130 which published on May 30, 2013 and is currently owned by Siemens Healthcare Diagnostics, Inc. (the contents of which are hereby expressly incorporated in their entirety herein by reference). Also, if desired, multiple components may be disposed together in a single formulation and/or lyophilized in a single particle.

The relative amounts of the various components/reagents in the reaction vessels can vary widely to provide for concentrations of the components/reagents that substantially optimize the reactions that need to occur during the assay methods and further to substantially optimize the sensitivity of the assay(s). Under appropriate circumstances, one or more of the components/reagents in the vessel can be provided in a dry form, such as a lyophilized particle, including, without limitation, spheres, micro-tablets, powders, micro-spots, combinations thereof, and/or the like.

The reaction vessel(s) may have one or more manual functions associated therewith, including, without limitation, pipetting to either add one or more reagents or samples and/or to move a mixture between two or more compartments of the device. Alternatively, or in addition to, the reaction vessel(s) may be a fully automatic, closed system in which the necessary reagents/components are disposed in various compartments during the construction of the vessel(s), wherein the various compartments are in continuous fluidic communication (or are capable of being in continuous fluidic communication), and thus no manual manipulation of the sample and/or reagent(s) is required for performance of the one or more assays after the sample is added to the reaction vessel(s).

In a non-limiting embodiment, the reaction vessel(s) utilized in accordance with the presently disclosed and/or claimed inventive concept(s) comprises one or more compartments containing the components described herein above; the reaction vessel(s) may be provided with any number of compartments, any arrangement of compartments, and any distribution of the components therebetween, so long as the vessel(s) is able to function in accordance with the presently disclosed and/or claimed inventive concepts. When provided with multiple compartments, the compartments may be completely separated from one another, or one or more compartments may be capable of being fluidic communication with one another. Various structures of reaction vessel(s) that are capable of use in accordance with the presently disclosed and/or claimed inventive concept(s) as well known in the art (as previously disclosed herein), and therefore no further description thereof is deemed necessary.

In certain non-limiting embodiments, the reaction vessel(s) may include at least two compartments capable of being in fluidic communication with one another, and the at least one diagnostic assay reagent (for instance, by way of example, at least one immunoassay reagent) may disposed in the same or different compartments.

The reaction vessel(s) may further include a sample application chamber and/or an inlet channel in which a patient's liquid test sample (for instance, by way of example, a patient's urine sample) may be applied or disposed within. The sample application chamber/inlet channel may be capable of being in fluidic communication with the one or more compartments of the reaction vessel(s). In addition, when the reaction vessel(s) is provided with both a sample application chamber and an inlet channel, the sample application chamber may be capable of being in fluidic communication with the inlet channel, and the inlet channel may be capable of being in fluidic communication with the one or more compartments in which the diagnostic assay (e.g., immunoassay) reagents are disposed.

In certain embodiments, the reaction vessel(s) may comprise at least a first compartment and a second compartment. The first compartment is capable of receiving a biological sample and, if desired, at least one buffer for providing an optical blank during the conductance of at least diagnostic assay and/or for mixing with the patient's liquid test sample and facilitating the transport of the sample between the first and second compartments. The second compartment is capable of being in fluidic communication with the first compartment and includes the at least one diagnostic assay reagent (such as, by way of example, at least one immunoassay reagent). Alternatively, the reaction vessel(s) may comprise a third compartment, wherein the third compartment is in fluidic communication with the first compartment, the second compartment, or both, and the third compartment may comprise at least one diagnostic assay reagent for conducting at least one diagnostic assay and/or at least one diagnostic assay reading and/or measurement.

The reaction vessel(s) may further comprise at least one optical read window that is capable of being optically interrogated by an optical source, for instance, by way of example only, a spectrophotometer, a fluorometer, and/or a nephelometer, to thereby measure certain characteristics associated with the patient's liquid test sample (both before and after the patient's liquid test sample reacts with the at least one diagnostic assay reagent). The at least one optical read window may be located within any of the compartments described hereinabove, or the optical read window(s) may be located within a separate compartment from those described hereinabove.

Any of the compartments of the reaction vessel(s) may be sealed to maintain the diagnostic reagent(s) disposed therein in a substantially air tight environment until use thereof. For example, compartments containing lyophilized reagent(s) (for instance, within a reaction zone(s) located in such compartment(s)) may be sealed to prevent unintentional reconstitution of the reagent(s). The inlet channel and the at least one compartment, as well as the two and/or three compartments described hereinabove, may be described as being "capable of being in fluidic communication" with one another, which means that the compartment(s) may be sealed, but the two (or three) compartments are capable of having fluid flow therebetween upon the introduction of the patient's liquid test sample, diagnostic assay buffer, and/or at least one liquid diagnostic assay reagent.

The reaction vessel(s) of the presently disclosed and/or claimed inventive concept(s) may be provided with any other desired features known in the art or otherwise contemplated herein. For example, but not by way of limitation, the reaction vessel(s) of the presently disclosed and/or claimed inventive concept(s) may further include one or more additional compartments containing other solutions, such as, but not limited to, diluents, wash solutions, buffers, lysing agents (for lysing red blood cells), excipients (utilized for reconstitution of lyophilized reagents), labeling agents, interference solutions, positive controls, negative controls, quality controls, and/or actuators, as well as any combinations thereof. For example, the reaction vessel(s) may include one or more additional compartments containing a diluent, and these additional compartment(s) may be capable of being in fluidic communication with any other compartment(s) of the reaction vessel(s). In another non-limiting example, the reaction vessel(s) may further include one or more additional compartments containing at least one excipient for reconstitution of one or more lyophilized reagents, and the additional compartment(s) may be capable of being in fluidic communication with any other compartment(s)/channel(s) of the reaction vessel(s) (such as any compartment containing lyophilized reagent(s)). In addition, the reaction vessel(s) may include one or more additional compartments containing a wash solution and/or buffer, and the compartment(s) may be capable of being in fluidic communication with any other compartment(s)/channel(s) of the reaction vessel(s).

Any of the reaction vessel(s) described or otherwise contemplated herein may include multiple diagnostic assays (such as, by way of example only, multiple immunoassays) multiplexed in a single reaction vessel. When multiple assays are present, the multiple assays may be constructed and function as described herein. Alternatively, an assay as described herein may be multiplexed with any other type of assay known in the art that is capable of being contained within the reaction vessel(s) of the presently disclosed and/or claimed inventive concept(s). When multiple assays are present in a single reaction vessel, the multiple assays may be run simultaneously and/or sequentially (including wholly or partially sequentially). When multiple assays are run simultaneously, it may be desired to utilize two or more diagnostic assay reagents (such as, by way of example, two or more detection reagents) that are detected at different masses and/or wavelengths.

Experimental Data

Experimental data generated from the presently disclosed and/or claimed inventive concept(s) is presented hereinbelow. However, the presently disclosed and/or claimed inventive concept(s) is to be understood to not be limited in its application to the specific experimentation, results, and laboratory procedures performed. Rather, the experimental data and/or example(s) are simply provided as one of various embodiments and are meant to be exemplary, not exhaustive.

Microalbumin Hook Detection Method(s)

Current immunoassay analyzers, such as, by way of example only, DCA Vantage® analyzers commercially offered for sale by Siemens Healthcare Diagnostics, Inc., collect microalbumin absorbance readings after reagent mixing is complete and calculates microalbumin concentration using only end-point/final-point microalbumin absorbance.

In performing the methodology(-ies) of the presently disclosed and/or claimed inventive concept(s), at least two additional microalbumin sample absorbance readings are measured and recorded, the at least two additional microalbumin sample absorbance readings being taken early during the microalbumin reagent mix cycle to monitor the progress of the immunoassay reaction(s). These early readings facilitate the monitoring of the reaction kinetics for the microalbumin immunoassay reaction(s), which are different for hook and non-hook samples. Samples exhibiting the hook effect show an initially higher absorbance with a more gradual absorbance increase thereafter as related to sample that do not exhibit the hook effect.

Figure 2:
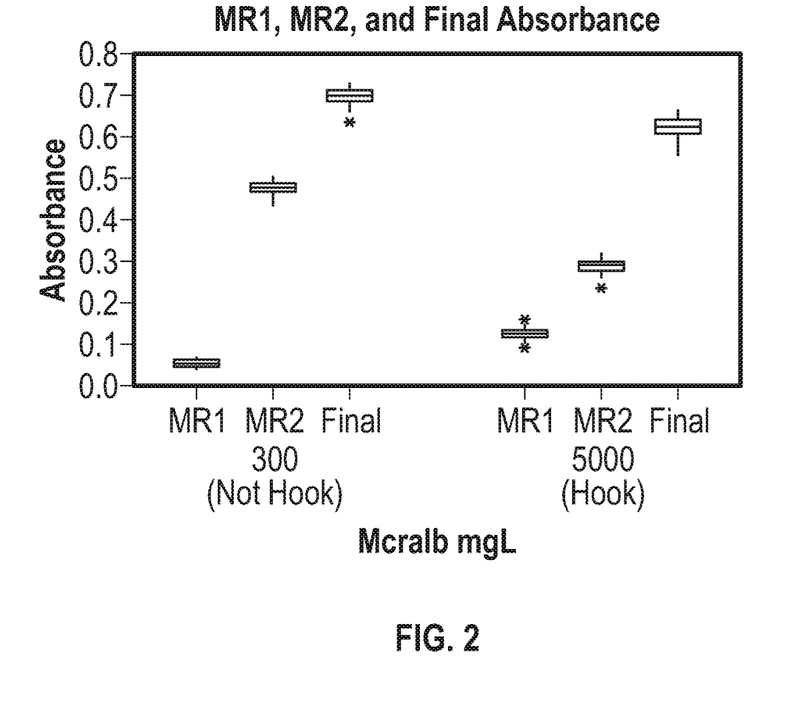
FIG. 2 is a graphical representation of three absorbance measurements taken for a microalbumin sample exhibiting the hook effect and three absorbance measurements taken at the same times for a microalbumin sample that does not exhibit the hook effect.

As shown in FIG. 2, a first absorbance measurement (represented as MR1), a second absorbance measurement (MR2), and a final absorbance measurement (represented as MCR or final) were obtained from conducting immunoassays in accordance with the presently disclosed and/or claimed inventive concept(s) on two different microalbumin samples—a non-hook microalbumin sample comprising a known concentration of 300 milligrams/liter of microalbumin and a hook microalbumin sample comprising a known concentration of 5,000 milligrams/liter of microalbumin. As shown in FIG. 2, the hook microalbumin sample shows an elevated MR1 absorbance when compared to the MR1 of the non-hook microalbumin sample, followed by a more gradual increase in absorbance (for both the MR2 and final absorbance readings) when compared to the non-hook microalbumin sample.

Utilizing the data generated from FIG. 2, a formula/algorithm has been developed to determine when a sample is exhibiting a hook effect with respect to microalbumin concentration (without the need to conduct a secondary test to confirm the findings). In one non-limiting embodiment, a sample is exhibiting the hook effect with respect to microalbumin if the conditions of the following formula/algorithm are satisfied:

IF (Microalbumin result is ≥200 milligrams/liter)
AND $((MCR-MR2)/(MR2-MR1)>1)$     [3]

As previously mentioned, MCR represents the final absorbance of the microalbumin sample. The hook effect levels out at extreme concentrations, and microalbumin samples with microalbumin concentration up to 10,000 milligrams/liter did not produce results less than 200 milligrams/liter (which thus justified setting the microalbumin concentration of 200 milligrams/liter as the bottom threshold for formula/algorithm fidelity). Moreover, while a predetermined concentration of 200 milligrams/liter was utilized as the predetermined target analyte (in this case, microalbumin) concentration threshold, a person having ordinary skill in the art should readily appreciate (and as additionally described elsewhere herein) that this predetermined threshold concentration is not limited to 200 milligrams/liter and can be any concentration capable of accomplishing the presently disclosed and/or claimed inventive concept(s).

Figure 3:
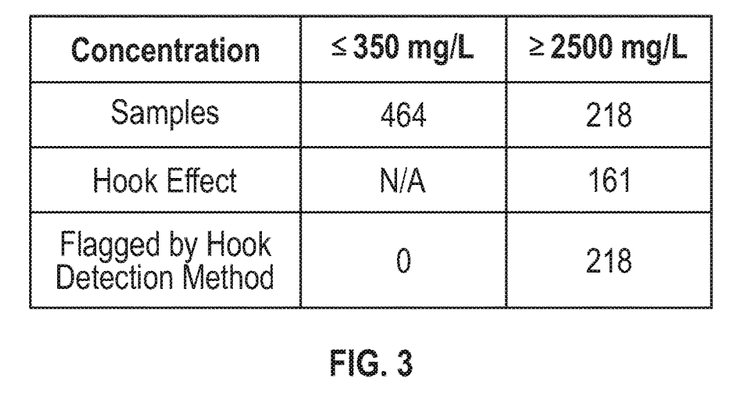
FIG. 3 is a table depicting the statistical information generated from running a number of microalbumin samples of various concentrations via utilization of detection formula(s)/algorithm(s) of the presently disclosed and/or claimed inventive concept(s).

FIG. 3 depicts the results obtained from testing detection formula/algorithm [1] detailed hereinabove. As shown in FIG. 3, of 464 samples with microalbumin concentrations in or near the assay range (i.e., from about 0 milligrams/liter to about 350 milligrams/liter), none of the 464 samples were flagged by the detection formula/algorithm [3] as exhibiting the hook effect. Conversely, of 218 samples with very high microalbumin concentrations (i.e., from about 2,500 milligrams/liter to about 5,000 milligrams/liter), all 218 samples were flagged as exhibiting the hook effect by the detection formula/algorithm [3]. Without performing the detection formula/algorithm [3] on these 218 samples, 161 of these samples would have produced a false result, showing an erroneous final microalbumin concentration of less than about 300 milligrams/liter due to the hook effect.

Detection formula/algorithm [3] can be hardcoded in the diagnostic assay analyzer's software. Alternatively (or in addition to), specific numbers associated with the detection formula/algorithm [3] may be included on the reagent barcode if necessary to allow for variation for lot of reagent(s) (for instance, it may be programmed that only samples yielding concentrations >300 milligrams/liter would be identified as samples exhibiting the hook effect).

Figure 4:
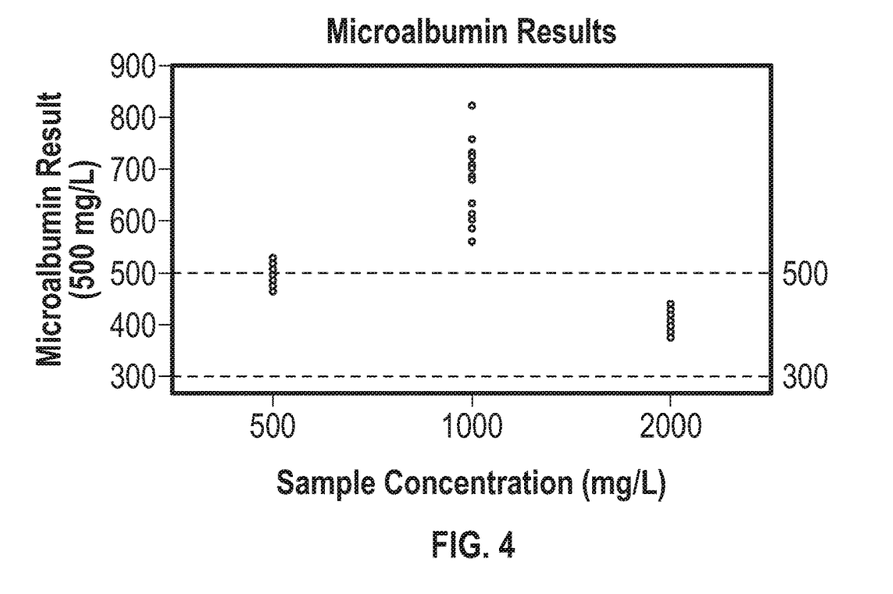
FIG. 4 is a graphical representation of the microalbumin results obtained for a number of microalbumin samples in which the microalbumin result of 500 milligrams/liter is plotted against microalbumin sample concentration result.
Figure 5:
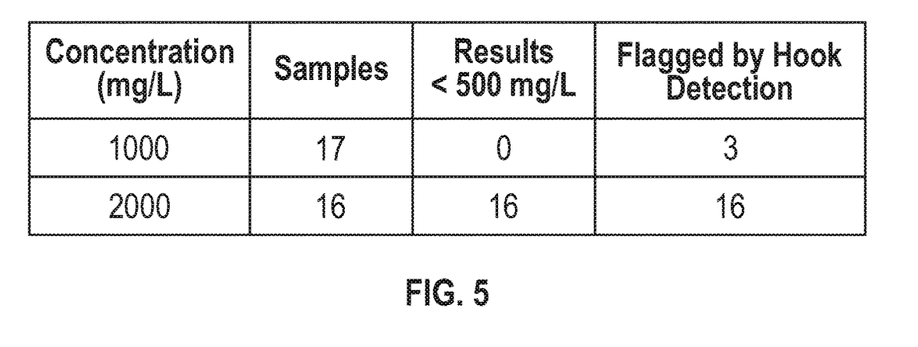
FIG. 5 is a table depicting the results of samples exhibiting the hook effect via utilization of detection formula(s)/algorithm(s) of the presently disclosed and/or claimed inventive concept(s) for samples having microalbumin concentrations of 1,000 milligrams/liter or 2,000 milligrams/liter.

For common diagnostic assay analyzers, the assay range for microalbumin ends at around 300 milligrams/liter, such that samples containing microalbumin concentrations of about 2,000 milligrams/liter do not exhibit the hook effect within the assay range. As shown in FIGS. 4 and 5, the detection formula/algorithm [3] may allow the assay range to be extended, for instance, up to a microalbumin concentration of about 500 milligrams/liter. Samples having a microalbumin concentration of 2,000 milligrams/liter produce erroneous results (due to the hook effect) of less than 500 milligrams/liter; however, these samples producing erroneous results due to the hook effect can be reliably identified by the detection formula/algorithm [3]. In addition, as shown in FIGS. 4 and 5, samples having a microalbumin concentration of 1,000 milligrams/liter did not produce results within the expanded assay range of less than 500 milligrams/liter.

NON-LIMITING EXAMPLES OF THE INVENTIVE CONCEPT(S)

Certain non-limiting embodiments of the presently disclosed and/or claimed inventive concept(s) include, but are not limited to the following:

A method for determining the presence of a hook effect in a patient's liquid test sample to determine the accuracy of concentration measurements of at least one target analyte of interest present within the patient's liquid test sample, the method comprising the steps of: conducting at least one diagnostic assay on a patient's liquid test sample within a diagnostic assay reaction vessel of a diagnostic assay system to determine the concentration of at least one target analyte of interest present in the patient's liquid test sample, wherein during the conductance of the at least one diagnostic assay, at least a first absorbance measurement (MR1) of the patient's liquid test sample, a second absorbance measurement (MR2) of the patient's liquid test sample, and a final absorbance measurement (MRC) of the patient's liquid test sample are recorded via optical interrogation of the patient's liquid test sample; determining a final concentration result of the at least one target analyte associated with the MRC of the patient's liquid test sample; establishing whether the final concentration result of the at least one target analyte exceeds a predetermined concentration value; and if the final concentration result of the at least one target analyte exceeds a predetermined concentration value, determining the presence of a hook effect associated with the at least one target analyte of interest present in the patient's liquid test sample by utilizing the MR1, MR2, and MRC in a detection formula, the detection formula comprising the following: IF (the at least one target analyte's concentration result is ≥C) AND ((MCR−MR2)/(MR2−MR1)>R), THEN the at least one target analyte of interest present in the patient's liquid test sample is subject to the hook effect, wherein C is the predetermined concentration value, and R is a predetermined limit for a ratio value to assess reaction kinetics of the at least one diagnostic assay, further wherein at least one result of the detection formula is output to a user.

The method, wherein the patient's liquid test sample is urine.

The method, wherein the at least one target analyte of interest is selected from the group selected from a peptide, a protein, and combinations thereof.

The method, wherein the at least one target analyte of interest is microalbumin.

The method, wherein the optical interrogation is performed by an optical device selected from the group consisting of a spectrophotometer, a fluorometer, and a nephelometer.

The method, wherein the at least one diagnostic assay is an immunoassay.

The method, wherein the predetermined concentration value is a value selected from a range of from about 0 milligrams/liter to about 500 milligrams/liter.

The method, wherein the predetermined concentration value is a value selected from a range of from about 0 milligrams/liter to about 300 milligrams/liter.

The method, wherein the diagnostic assay reaction vessel comprises a reaction cassette for use within a diagnostic analyzer.

The method, wherein the reaction cassette comprises at least two compartments, wherein each of the at least two compartments comprise at least one diagnostic assay reagent.

The method, wherein the at least one diagnostic assay reagent comprises an antibody.

The method, wherein the at least one antibody is an antibody of microalbumin.

The method, wherein the reaction vessel comprises at least one optical read window, and further wherein the optical interrogation occurs within the at least one optical read window.

The method, wherein the user is at least one computer functionally connected to the diagnostic assay system, and further wherein the detection formula is stored in non-transient memory of the at least one computer.

The method, wherein the output to the user is a notice that the at least one result of the detection formula indicates that the at least one target analyte of interest is subject to the hook effect, thereby allowing the user to conduct subsequent analyses on the patient's liquid test sample to determine an accurate concentration of the at least one target analyte of interest present in the patient's liquid test sample.

A method for determining the presence of a hook effect in a patient's liquid test sample to determine the accuracy of concentration measurements of at least one target analyte of interest present within the patient's liquid test sample, the method comprising the steps of: conducting at least one diagnostic assay on a patient's liquid test sample within a diagnostic assay reaction vessel of a diagnostic assay system to determine the concentration of at least one target analyte of interest present in the patient's liquid test sample, wherein during the conductance of the at least one diagnostic assay, at least a first absorbance measurement (MR1) of the patient's liquid test sample and a second absorbance measurement (MR2) of the patient's liquid test sample are recorded via optical interrogation of the patient's liquid test sample; determining a concentration result of the at least one target analyte associated with the MRC of the patient's liquid test sample; establishing whether the concentration result of the at least one target analyte exceeds a predetermined concentration value; and if the concentration result of the at least one target analyte exceeds a predetermined concentration value, determining the presence of a hook effect associated with the at least one target analyte of interest present in the patient's liquid test sample by utilizing the MR1 and MR2 in a detection formula, the detection formula comprising the following: IF (Target Analyte Concentration is ≥C) AND (MR1/MR2)>R, THEN the at least one target analyte of interest present in the patient's liquid test sample is subject to the hook effect, wherein C is the predetermined concentration value, and R is a predetermined limit for a ratio value to assess reaction kinetics of the at least one diagnostic assay, further wherein at least one result of the detection formula is output to a user.

The method, wherein the patient's liquid test sample is urine.

The method, wherein the at least one target analyte of interest is selected from the group selected from a peptide, a protein, and combinations thereof.

The method, wherein the at least one target analyte of interest is microalbumin.

The method, wherein the at least one diagnostic assay is an immunoassay.

Thus, in accordance with the presently disclosed and claimed inventive concept(s), there have been provided devices and methods that allow for hook effect detection associated with an analyte(s) of interest during or resulting from the conductance of diagnostic assays. As described herein, the presently disclosed and claimed inventive concept(s) relate to embodiments of an improved detection method which utilizes a formula to detect the presence or non-presence of the hook effect associated with an analyte of interest (such as by way of example, microalbumin) during or resulting from the conductance of at least one diagnostic assay (including, but not limited to, at least one immunoassay). Such presently disclosed and/or claimed inventive concept(s) fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A method for determining the presence of a hook effect in a patient's liquid test sample to determine the accuracy of concentration measurements of at least one target analyte of interest present within the patient's liquid test sample, the method comprising the steps of:

conducting at least one diagnostic assay on a patient's liquid test sample within a diagnostic assay reaction vessel of a diagnostic assay system to determine the concentration of at least one target analyte of interest present in the patient's liquid test sample, wherein during the conductance of the at least one diagnostic assay, at least a first absorbance measurement (MR1) of the patient's liquid test sample, a second absorbance measurement (MR2) of the patient's liquid test sample, and a final absorbance measurement (MRC) of the patient's liquid test sample are recorded via optical interrogation of the patient's liquid test sample, wherein MR1, MR2, and MRC are taken under the same measurement conditions but at different times such that MR1 is taken at a first time ($T_1$), MR2 is taken at a second time ($T_2$), and MRC is taken at a conclusion of the diagnostic assay, and wherein $T_1$ and $T_2$ each occur after a time when the patient's liquid test sample is mixed with an assay reagent and before a time when the diagnostic assay reaches its final absorbance, whereby $T_1$, $T_2$, and MRC monitor reaction kinetics of the at least one diagnostic assay;

determining a final concentration result of the at least one target analyte associated with the MRC of the patient's liquid test sample;

establishing whether the final concentration result of the at least one target analyte exceeds a predetermined concentration value; and if the final concentration result of the at least one target analyte exceeds a predetermined concentration value, determining the presence of a hook effect associated with the at least one target analyte of interest present in the patient's liquid test sample by utilizing the MR1, MR2, and MRC in a detection formula, the detection formula comprising the following:

IF (the at least one target analyte's concentration result is ≥ C) AND ((MCR-MR2)/(MR2-MR1) >R), THEN the at least one target analyte of interest present in the patient's liquid test sample is subject to the hook effect, wherein C is the predetermined concentration value, and R is a predetermined limit for a ratio value to assess reaction kinetics of the at least one diagnostic assay, further wherein at least one result of the detection formula is output to a user.

2. The method of claim 1, wherein the patient's liquid test sample is urine.

3. The method of claim 1, wherein the at least one target analyte of interest is selected from the group selected from a peptide, a protein, and combinations thereof.

4. The method of claim 3, wherein the at least one target analyte of interest is microalbumin.

5. The method of claim 1, wherein the optical interrogation is performed by an optical device selected from the group consisting of a spectrophotometer, a fluorometer, and a nephelometer.

6. The method of claim 1, wherein the at least one diagnostic assay is an immunoassay.

7. The method of claim 1, wherein the predetermined concentration value is a value selected from a range of from about 0 milligrams/liter to about 500 milligrams/liter.

8. The method of claim 1, wherein the predetermined concentration value is a value selected from a range of from about 0 milligrams/liter to about 300 milligrams/liter.

9. The method of claim 1, wherein the diagnostic assay reaction vessel comprises a reaction cassette for use within a diagnostic analyzer.

10. The method of claim 9, wherein the reaction cassette comprises at least two compartments, wherein each of the at least two compartments comprise at least one diagnostic assay reagent.

11. The method of claim 10, wherein the at least one diagnostic assay reagent comprises an antibody.

12. The method of claim 11, wherein the at least one antibody is an antibody of microalbumin.

13. The method of claim 1, wherein the reaction vessel comprises at least one optical read window, and further wherein the optical interrogation occurs within the at least one optical read window.

14. The method of claim 1, wherein the user is at least one computer functionally connected to the diagnostic assay system, and further wherein the detection formula is stored in non-transient memory of the at least one computer.

15. The method of claim 1, wherein the output to the user is a notice that the at least one result of the detection formula indicates that the at least one target analyte of interest is subject to the hook effect, thereby allowing the user to conduct subsequent analyses on the patient's liquid test sample to determine an accurate concentration of the at least one target analyte of interest present in the patient's liquid test sample.

16. A method for determining the presence of a hook effect in a patient's liquid test sample to determine the accuracy of concentration measurements of at least one target analyte of interest present within the patient's liquid test sample, the method comprising the steps of:

conducting at least one diagnostic assay on a patient's liquid test sample within a diagnostic assay reaction vessel of a diagnostic assay system to determine the concentration of at least one target analyte of interest present in the patient's liquid test sample, wherein during the conductance of the at least one diagnostic assay, at least a first absorbance measurement (MR1) of the patient's liquid test sample and a second absorbance measurement (MR2) of the patient's liquid test sample are recorded via optical interrogation of the patient's liquid test sample, wherein MR1 and MR2 are taken under the same measurement conditions but at different times such that MR1 is taken at a first time ($T_1$) and MR2 is taken at a second time ($T_2$), and wherein $T_1$ and $T_2$ each occur after a time when the patient's liquid test sample is mixed with an assay reagent and before a time when the diagnostic assay reaches its final absorbance, whereby $T_1$ and $T_2$ monitor reaction kinetics of the at least one diagnostic assay;

determining a concentration result of the at least one target analyte associated with the MR2 of the patient's liquid test sample;

establishing whether the concentration result of the at least one target analyte exceeds a predetermined concentration value; and if the concentration result of the at least one target analyte exceeds a predetermined concentration value, determining the presence of a hook effect associated with the at least one target analyte of interest present in the patient's liquid test sample by utilizing the MR1 and MR2 in a detection formula, the detection formula comprising the following:

IF (Target Analyte Concentration is >C) AND (MR1/MR2)>R, THEN the at least one target analyte of interest present in the patient's liquid test sample is subject to the hook effect, wherein C is the predetermined concentration value, and R is a predetermined limit for a ratio value to assess reaction kinetics of the at least one diagnostic assay, further wherein at least one result of the detection formula is output to a user.

17. The method of claim 16, wherein the patient's liquid test sample is urine.

18. The method of claim 16, wherein the at least one target analyte of interest is selected from the group selected from a peptide, a protein, and combinations thereof.

19. The method of claim 18, wherein the at least one target analyte of interest is microalbumin.

20. The method of claim 16, wherein the at least one diagnostic assay is an immunoassay.

* * * * *